United States Patent
Irani (10) Patent No.: US 10,126,287 B2
(45) Date of Patent: Nov. 13, 2018

(54) MIXING FLUIDS WITH WEIGHTED AQUEOUS PHASES

(71) Applicant: HALLIBURTON ENERGY SERVICES, INC., Houston, TX (US)

(72) Inventor: Cyrus Aspi Irani, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 224 days.

(21) Appl. No.: 15/305,454

(22) PCT Filed: Sep. 18, 2014

(86) PCT No.: PCT/US2014/056279
§ 371 (c)(1),
(2) Date: Oct. 20, 2016

(87) PCT Pub. No.: WO2016/043746
PCT Pub. Date: Mar. 24, 2016

(65) Prior Publication Data
US 2017/0045490 A1  Feb. 16, 2017

(51) Int. Cl.
| | | |
|---|---|---|
| *G01N 33/00* | (2006.01) | |
| *G01N 33/24* | (2006.01) | |
| *E21B 49/08* | (2006.01) | |
| *B01F 3/08* | (2006.01) | |
| *B01F 11/00* | (2006.01) | |

(52) U.S. Cl.
CPC ........... *G01N 33/24* (2013.01); *B01F 3/0803* (2013.01); *B01F 11/00* (2013.01); *E21B 49/08* (2013.01); *E21B 49/081* (2013.01); *B01F 2215/0037* (2013.01)

(58) Field of Classification Search
None
See application file for complete search history.

(56) References Cited

U.S. PATENT DOCUMENTS

| | | |
|---|---|---|
| 2005/0087001 A1 | 4/2005 | Irani et al. |
| 2007/0265171 A1 | 11/2007 | Javora et al. |
| 2009/0151937 A1 | 6/2009 | Goodwin et al. |
| 2010/0269579 A1 | 10/2010 | Lawrence et al. |
| 2012/0149604 A1 | 6/2012 | Lawrence et al. |
| 2013/0306521 A1 | 11/2013 | O'Rear et al. |
| 2013/0315027 A1 | 11/2013 | Ringgenberg |

OTHER PUBLICATIONS

European Patent Application No. 14902178.4, "Partial Supplementary European Search Report", dated Oct. 9, 2017, 12 pages.
International Patent Application No. PCT/US2014/056279, International Search Report and Written Opinion, dated May 29, 2015, 15 pages.

*Primary Examiner* — Xiaoyun R Xu
(74) *Attorney, Agent, or Firm* — Kilpatrick Townsend & Stockton LLP (57) ABSTRACT

Methods of mixing fluids, especially wellbore fluids, without causing wear to the vessel containing the fluid, are disclosed, using weighted aqueous phase for mixing. Also disclosed are methods of mixing and analyzing fluids using weighted phases including scavengers.

19 Claims, 3 Drawing Sheets

MIXING FLUIDS WITH WEIGHTED AQUEOUS PHASES

CROSS-REFERENCE TO RELATED APPLICATIONS

This is a U.S. national phase under 35 U.S.C. 371 of International Patent Application No. PCT/US2014/056279, titled "Mixing Fluids with Weighted Aqueous Fluids" and filed Sep. 18, 2014, the entirety of which is incorporated herein by reference.

TECHNICAL FIELD

The present disclosure relates generally to the sampling of subterranean deposits and more specifically to methods and systems for preserving and analyzing fluid from a wellbore to determine the concentration of certain species whose presence may significantly impact operational, environmental, safety, and/or health considerations.

BACKGROUND

Wells are drilled at various depths to access and produce oil, gas, minerals, and other naturally-occurring deposits from subterranean geological formations. As wells are established it is often useful to obtain information about the well, the geological formations through which the well passes, and the fluid in the wellbore, including the fluid to be extracted from the formations. Information gathering is typically performed using tools that are delivered downhole by wireline, often referred to as wireline formation testing ("WFT"), or alternatively by tools that are coupled to or integrated into the drill string, either measuring while drilling ("MWD") or logging while drilling ("LWD"). Tools also can be delivered downhole on pipe or tubing during Drill Stem Testing ("DST") operations. It is often desired to collect a representative sample of formation or reservoir fluids (typically hydrocarbons) to further evaluate drilling operations and production potential, or to detect the presence of certain gases or other materials in the formation that may affect well performance.

Preservation of samples is an important aspect of well drilling. Samples may be collected at the surface or at any point downhole. Efforts are made to collect a representative sample and to maintain the sample in a representative state throughout the recovery, transfer, storage, and eventual analysis. Maintenance of the representative state is particularly significant when the sample contains trace amounts of species whose accurate determination may significantly impact operational, environmental, safety, and/or health considerations. Typical, non-limiting examples of such species include hydrogen sulfide and mercury. Hydrogen sulfide ("$H_2S$") is a poisonous, corrosive, and flammable gas that can occur in formation fluids, and its presence in the wellbore in significant concentrations may result in damage to wellbore components or dangerous conditions for well operators at the surface. Thus, operational considerations are greatly impacted by the location and concentration of the $H_2S$ in the produced reservoir stream. Far different procedures and equipment are required depending on whether the concentration is 2 ppm, 20 ppm, or 200 ppm and higher.

Sample vessels and long term storage vessels typically are constructed using stainless steel or austenitic nickel-chromium-based superalloys (such as those sold under the Inconel™ name) because of their availability and raw material costs, but may be constructed of more exotic and costly materials, such as cobalt or titanium. Most common metallurgies adsorb certain amounts of trace components. For example, in about a week's time, and usually less, a sample taken from a fluid stream containing 15 ppm $H_2S$ may show no $H_2S$, when analyzed. However, when put into service, this field will deliver 15 ppm $H_2S$. Operationally, the facility will not be properly geared to handle the actual level because none was detected in the analyzed sample. This shortcoming can have significant safety, health, environmental, operational, and cost implications.

Vessels may be coated to minimize or eliminate the adsorption and accompanying complications. Examples of such coatings include silicon-based Sulfinert™ treatments and ceramic-based Tech-12™ treatments. The coatings are usually fired at about 800° F. and leave behind about a one micron layer that fills the pore spaces available for $H_2S$ adsorption to minimize or eliminate the problem. Because of their very thin nature, these coatings are susceptible to erosion, especially during any mixing steps required for transferring or analyzing a representative sample.

Conventionally, mixing is accomplished with mixing balls or mixing rings placed inside the sample or storage vessel, such that when the container is rocked, the resulting lateral movement of the balls or rings results in the mixing of the contents. To be effective, especially within the context of viscous oils or low API value heavy oils, the mixing mechanism needs to be heavy enough to transition the sample space during the rocking action. A direct consequence of the heavy solid element moving vigorously across the inner face of a coated vessel is undesirable erosion of any applied protective coating, the loss of which results in the adsorption of certain species and subsequent analysis of a non-representative sample.

There is an ongoing need for an alternative means of mixing that is not destructive to the applied coating and that allows for analysis of representative samples. The methods and systems described herein are directed to these as well as other important ends.

GLOSSARY

As employed above and throughout the disclosure, the following terms, unless otherwise indicated, shall be understood to have the following meanings.

As used herein, the singular forms "a," "an," and "the" include the plural reference unless the context clearly indicates otherwise.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various aspects.

As used herein, "inert" refers to a material that has little or no ability to react with the other components in a mixture to which it is added, especially in the time frame and under the pressure and temperature conditions under which they are mixed.

As used herein, the term "solution" refers to a homogeneous mixture of two or more materials where the material is composed of only one phase, and where a solute is the material dissolved in another material (the solvent).

As used herein, the term "colloid" refers to a mixture of two or more materials where one material is microscopically dispersed throughout another material. Unlike a solution, there is more than one phase, even if the different phases are not discernible to the naked eye.

With reference to a solution, the term "saturated" refers to a point of a maximum concentration, in which no more solute may be dissolved in a solvent. With reference to a solution, the term "supersaturated" refers to the state of a solution that contains more of the dissolved substance (solute) than could be dissolved by the solvent under normal circumstances, as for example in a saturated solution. Supersaturated solutions are prepared or result when some condition of a saturated solution is changed, for example increasing (or, rarely, decreasing) temperature, decreasing volume of the saturated solvent (as by liquid evaporation), or increasing pressure. When the term "saturated" is used herein with reference to a fluid comprising a weighted aqueous phase, it is meant to include "supersaturated," unless the context clearly indicates otherwise.

As used herein, "API gravity" refers to the American Petroleum Institute gravity, which is a relative density measurement that reflects how light or heavy a test fluid is (typically a crude oil or hydrocarbon liquid) compared to water. It is reported in degrees (°) and most oils fall within the range from about 10° to 70° API. If an oil's API gravity is greater than 10°, it is lighter than water and will float on it. If an oil's API gravity is less than 10°, it is heavier than water and will sink. The formula for calculating API gravity is:

$$\{(141.5 \div \text{relative density of the test fluid(at } 15.5° \text{ C. or } 60° \text{ F.})\} - 131.5$$

As used herein, "demulsifier" refers to active chemical intermediates that, when formulated into blends and applied in the field, reduce the interfacial tension between hydrocarbon and water, allowing for rapid coalescence, dehydration and separation of the liquid phases, which leads to improved quality of the separated hydrocarbon.

As used herein, the term "weighted" refers to a material, preferably a solution, that includes two or more components, wherein the weighted material has a density higher than the density of at least one of its constituent components or relative to the density of another material with which it will be combined. In the case of a solution, the solution is weighted if it has a density higher than that of its solvent. In that case, the solute may be referred to as the "weighting agent." For example, an aqueous sodium chloride solution has a higher density than pure water. Thus, the aqueous sodium chloride solution is weighted relative to the water and the sodium chloride is the "weighting agent." Furthermore, a saturated aqueous sodium chloride solution and a supersaturated aqueous sodium chloride solution are further weighted relative to the water from which they are made and are weighted relative to a dilute aqueous sodium chloride solution. While sodium chloride is used as the only weighting agent in these examples, a fluid may include more than one weighting agent.

As used herein, a "scavenger" is generally understood to be a chemical substance added to a mixture to remove or deactivate impurities or unwanted reaction products in the mixture, and a "scavenger volume" is a mass or volume of a scavenger material.

DETAILED DESCRIPTION

In the following disclosure, reference is made to illustrative aspects and accompanying drawings that form a part of the disclosure. While the disclosure is capable of being embodied in various forms, the description below of several compositions, methods, and systems is made with the understanding that any aspect disclosed is to be considered as an exemplification and is not intended to limit the disclosure to the aspects illustrated.

The systems and methods described herein provide for the preservation and analysis of formation fluids extracted from wells either during or after drilling operations. Methods are described in which formation fluids are collected for analysis and combined with denser, weighted fluids in a vessel, and the weighted fluids are used to mix the formation fluids without damaging the surface of the vessel and without damaging any coating on that surface. Methods described herein may be used, for example, to mix samples collected from a wellbore prior to testing. The sample may be collected at any point downhole or at the surface. The methods allow maintenance of the sample in its representative state and result in less wear on the vessel holding the sample as compared to prior methods of mixing that use solid mixing tools, such as mixing balls or rings. In some cases vessel wear may be eliminated entirely.

While the weighted aqueous fluid may be inert, also described herein are systems and methods which provide for the quantitative analysis of at least one component of a formation fluid using an additive or scavenger. The scavenger aids in maintaining a sample in its representative state by trapping, adsorbing, and/or reacting with impurities in a way that allows later quantitative analysis of the concentration of the impurity at the time the sample was collected.

The methods described herein thus generally involve using a weighted first fluid as a mixing media, sometimes referred to herein as a "mixing fluid," to efficiently mix a second fluid (e.g. a sample fluid) that includes two or more components or materials. The first fluid is weighted such that its density is higher than the density of the second fluid. In aspects the weighted fluid has an API gravity less than the API gravity of the fluid it is mixing. In aspects the weighted fluid has an API gravity less than about 10°, preferably less than about 9.0°, more preferably less than about 8.0°, even more preferably less than about 7.0°, and most preferably less than about 5.0°. The weighted fluid may be, for example, an aqueous salt solution or another weighted aqueous phase. When the weighted mixing fluid and sample fluid are combined in a vessel, the higher density of the weighted fluid allows the weighted fluid to transition through the vessel as the vessel is rocked and thereby mix the sample fluid. The higher relative density of the weighted fluid enables efficient mixing of any materials in the sample fluid.

In aspects, the weighted fluid is present at a level of about 1% by volume up to about 25% by volume, but may be present at much higher levels, up to about 50% by volume, 60% by volume, 70% by volume, 80% by volume, 90% by volume and even more, based on the total volume of the mixture of fluids.

In some aspects of the methods described herein, the weighted mixing fluid is water-based and is a saturated or supersaturated solution or colloid. The weighted aqueous phase may include as a weighting agent a salt, sugar, urea, glycerol, methylsulfonylmethane, or combinations thereof. Alternatively or additionally, the weighting agent may include a scavenger as discussed in detail below. Where the weighting agent is a salt, the salt may be any combination of cation and anion that is soluble in water. For example, in some aspects, the salt may be formed from a cation selected from $Na^{+1}$, $K^{+1}$, $Ca^{+2}$, $Zn^{+2}$, $Cs^{+2}$; and $Ba^{+2}$ and an anion selected from $SO_4^{-2}$, $Cl^{-1}$, $Br^{-1}$, $F^{-1}$, $I^{-1}$, and formate. In one aspect the salt may be, or may include, potassium bromide. Where the weighting agent is a sugar, the sugar may include a C5 saccharide, C6 saccharide, or combination thereof. A person skilled in the art can readily calculate the saturation point for any given solution.

The fluid that is mixed by the weighted fluid may be any fluid in need of mixing, but in some aspects is a formation fluid extracted from a wellbore. The formation fluid may include at least one hydrocarbon oil or gas, and in certain aspects the formation fluid includes crude oil. The formation fluid may further include any other materials naturally occurring in such fluid, including impurities in trace amounts. For example, some formation fluids include natural surfactants. Hydrogen sulfide and mercury are additional materials that may be found in formation fluids. Natural surfactants, $H_2S$, and mercury are only examples of materials that may be present in a formation fluid, and the disclosure is not limited to any particular materials.

In some aspects, the weighted fluid includes a demulsifier. As an example, emulsions can form in oil-water systems. The addition of the demulsifier minimizes the risk of the aqueous phase forming an emulsion in a fluid comprising an oil or gas due to the mixing action, especially in cases where the oils have natural surfactants present in them. Demulsifiers are typically acid catalyzed phenol-formaldehyde resins, base catalyzed phenol-formaldehyde resins, epoxy resins, polyethyleneimines, polyamines, di-epoxides, and polyols, which may be ethoxylated (and/or propoxylated) to provide the desired degree of water/oil solubility. The addition of ethylene oxide increases water solubility, and the addition of propylene oxide decreases it. Commercially available demulsifier formulations are typically a mixture of two to four different chemistries, in carrier solvent(s) such as xylene, heavy aromatic naphtha (HAN), isopropanol, methanol, 2-ethylhexanol or diesel.

In some aspects, the weighted fluid includes a defoamer. As an example, foams can form when the methods described herein are used to mix gas phases. The addition of a defoamer minimizes the risk of the aqueous phase forming a foam when it is used to mix a fluid comprising a gas phase. A defoamer may be oil or water based, is insoluble in the foaming medium, and has surface active properties. A combination of low viscosity and an ability to spread at gas-liquid interfaces causes a destabilization of foam lamellas, resulting in the rupture and breakdown of the foam structure. Silicone based defoamers are a significant class in themselves, and are primarily comprised of polydimethylsiloxanes and other silicones. A certain class of defoamers is oil based with the base oil represented by mineral oil, vegetable oil, or white oil, occasionally including additives like wax or hydrophobic silica to boost their performance. Water based defoamers exploit different kinds of oils and waxes dispersed in the water phase. Different applications will call for different types of defoamers, with the intent of destabilizing the multiple lamella that comprise a foam, allowing for a cleaner and more manageable liquid-gas interface.

In some aspects, after a weighted fluid effects mixing of a sample fluid, the weighted and sample fluids are separated. After separation, it may be possible to use the weighted fluid to mix another sample fluid. Separation of the fluids may be accomplished by any means known in the art for separating fluids. For example, the fluids may be separated by gravity-based separation techniques, chemical affinity-based separation techniques, or combinations thereof. As one example, in one aspect of the method, liquids may be separated by decantation by allowing the mixture of fluids to settle and separate by gravity and then pouring off the lighter, i.e., less dense, liquid leaving the heavier, i.e., more dense, liquid and any solids behind. Such separation may be aided by use of a centrifuge. As another example, in one aspect of the method, the fluids may be separated by filtration, including filtration through hydrophobic membranes, or by passing through zeolite mixtures. Other methods of separation include distillation, chromatography, adsorption, extraction, stripping, oil-water separation using an API oil-water separator, and any other separation technique known to one skilled in the art.

In some aspects, the sample fluid is hydrophobic and the mixing fluid is aqueous, thereby making it possible to separate the sample fluid and mixing fluid after the sample is collected, transported, stored, and prepared for testing. In some aspects, saturated salt solutions may be employed in the weighted mixing fluid to minimize or eliminate any solubility of the hydrophobic sample fluid in the mixing fluid because the aqueous-based mixing fluid has a strong salting out effect to a high concentration of salt.

The methods described herein are useful in the oilfield industry, as described herein, but are not limited to such use. For convenience herein, weighted aqueous phases are described as examples of the weighted, mixing fluid and formation fluids are described as examples of the fluid being mixed; however, the methods described herein could be carried out with other fluids and in other industries.

In one aspect, a formation fluid from a wellbore is combined with a weighted aqueous phase and the weighted aqueous phase is used to mix the components of the formation fluid. The weighted fluid replaces solid mixing tools, such as mixing balls or rings, that are known to damage the surface coating of sampling or storage vessels. Because using weighted fluids to mix the sample eliminates the need for solid mixing tools, damage to the surface of the sampling or storage vessel as a result of a mixing tool sliding across the vessel is reduced or eliminated and the useful life of the vessel is increased. Moreover, a liquid phase has greater mobility than a solid device and therefore can provide improved mixing over solid devices.

Figure 1A:
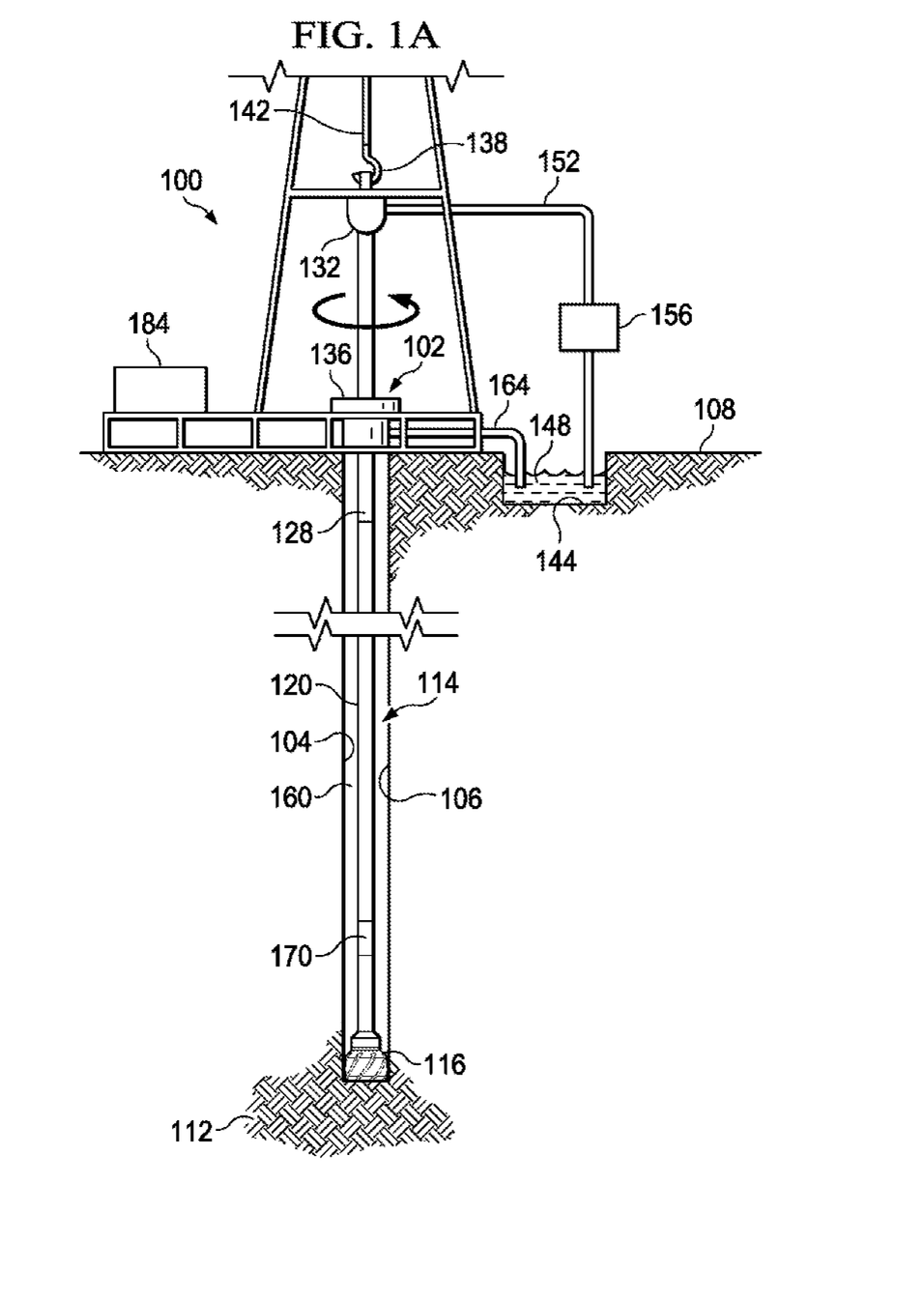
FIG. 1A illustrates a schematic view of a well in which a fluid sampling system is deployed in an LWD assembly.
Figure 1B:
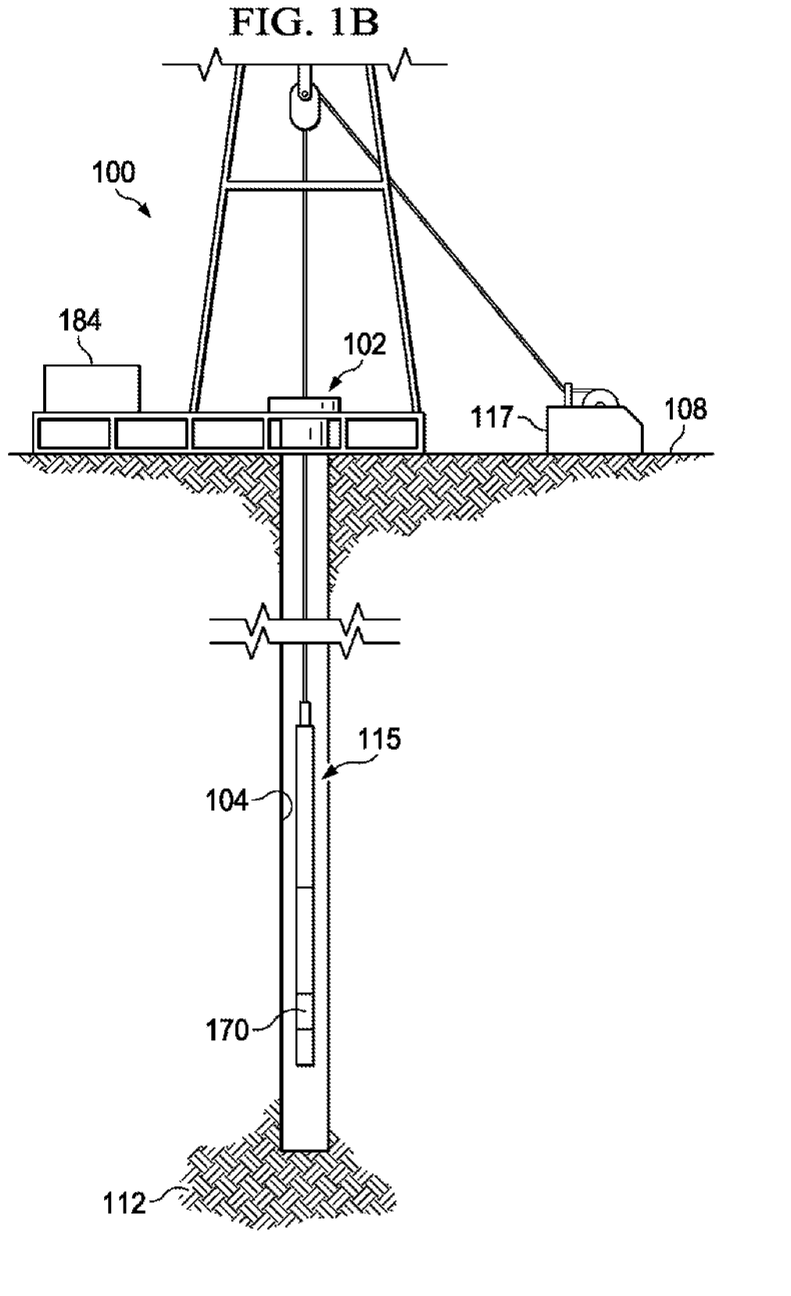
FIG. 1B illustrates a schematic view of a well in which the fluid sampling system of FIG. 1A is deployed on wireline as part of a WFT assembly.
Figure 1C:
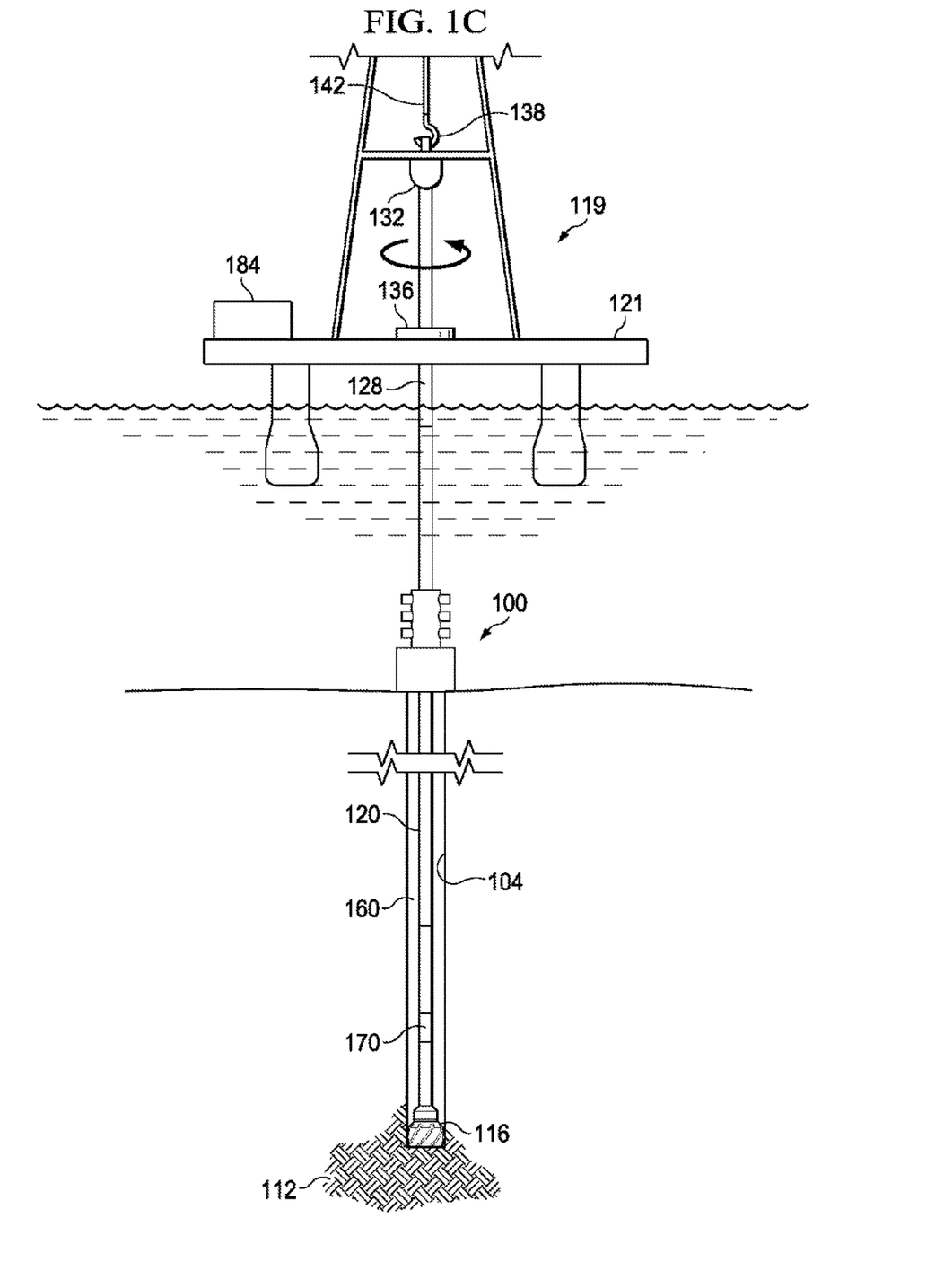
FIG. 1C illustrates a schematic view of a subsea well in which the fluid sampling system of FIG. 1A is deployed.

The compositions, methods, and systems described herein may be used with any of the various techniques employed for evaluating a well, including without limitation wireline formation testing (WFT), measurement while drilling (MWD), logging while drilling (LWD), and drill stem testing (DST). The formation fluid may be collected downhole during drilling or after a well is completed. Referring now to FIGS. 1A-1C, a fluid sampling and analysis system 100 is used in a well 102 having a wellbore 104 that extends from a surface 108 of the well to or through a subterranean geological formation 112. The well 102 is illustrated onshore in FIG. 1A with the fluid sampling and analysis system 100 being deployed in an LWD assembly 114. Alternatively, fluid sampling and analysis system 100 may instead be deployed as part of a wireline assembly 115 (see FIG. 1B), either onshore or offshore. The wireline assembly 115 includes a winch 117 to lift and lower a downhole portion of the wireline assembly 115 into the well. In still another aspect, the fluid sampling and analysis system 100 may be deployed in a sub-sea well 119 accessed by a fixed or floating platform 121. FIGS. 1A-1C each illustrate these possible uses of the fluid sampling and analysis system 100, and while the following description of the fluid sampling and analysis system 100 focuses primarily on the use of the fluid sampling and analysis system 100 with the LWD assembly 114 of FIG. 1A, the fluid sampling and analysis system 100 may be used instead in the well configurations illustrated in FIGS. 1B and 1C, as well as in other well configurations where it is desired to sample a fluid. Similar components in FIGS. 1A-1C are identified with similar reference numerals.

In the aspect illustrated in FIG. 1A, the well 102 is formed by a drilling process in which a drill bit 116 is turned by a drill string 120 that extends from the drill bit 116 to the surface 108 of the well 102. The drill string 120 may be made up of one or more connected tubes or pipes, of varying or similar cross-section. The drill string may refer to the collection of pipes or tubes as a single component, or alternatively to the individual pipes or tubes that comprise the string. The term drill string is not meant to be limiting in nature and may refer to any component or components that are capable of transferring rotational energy from the surface of the well to the drill bit. The drill string 120 may include a central passage disposed longitudinally in the drill string and capable of allowing fluid communication between the surface of the well and downhole locations.

A fluid sampling tool 170 may be positioned downhole to obtain fluid samples from the formation for analysis, and to measure, process, and communicate data regarding the formation, fluid from the formation, or other operations occurring downhole. This information, including information gathered from analysis of the fluid sample, allows well operators to determine, among other things, the concentration $H_2S$ within the fluid being extracted from the formation 112 to make intelligent decisions about ongoing operation of the well. While the fluid sampling tool 170 is illustrated as a part of the drill string 120 in FIG. 1A, in other aspects, the fluid sampling tool 170 may be lowered into the well by wireline (see FIG. 1B) either through the central passage of the drill string 120 or, if the drill string 120 is not present, directly through the wellbore 104.

One of skill in the art could adapt the disclosure herein for use with various sampling tools. As one example, in one method, a sample chamber is prepared for deployment into a well by inserting a weighted fluid into the sample vessel, which is in turn lowered into position in the wellbore, as shown in FIGS. 1A-1C. After taking a sample of the fluid, the fluid sampling device may be returned to the surface. In a wireline or slickline operation, this may be done immediately or almost immediately after the sample is taken. In a MWD, LWD or DST operation, the return to the surface may not happen until some reason occurs to withdraw the entire drill string from the borehole.

The weighted mixing fluid may be inserted into a sampling chamber of a sample collection device prior to deployment in the wellbore or may be combined with a formation fluid sample after the sample is collected. Similarly, the weighted mixing fluid may be inserted into a storage vessel prior to, or after, a sample of a formation fluid has been transferred from a sample collection tool to the storage vessel. If the collection or storage vessel is coated to prevent reaction between any material in the sample fluid and any part of the vessel, the vessel may be stored and/or transported off site prior to introduction of the mixing fluid.

The sample fluid may be mixed by rocking or otherwise moving the vessel containing the weighted mixing fluid and the sample fluid so as to cause the weighted mixing fluid to transition the sample space and mix the components of the sample fluid. "Rocking" includes moving the vessel back and forth, from side to side, and/or in a see-saw motion. The rocking may be accomplished by manual movement of the vessel, or alternatively by a mechanical rocking device, any number of which are available and well known to one skilled in the art. Depending on the circumstances, the rocking action might be implemented anywhere from two hours to one week. Alternatively, the After mixing and separation, the sample fluid may be analyzed by a number of means at any convenient location. By far the most common analysis a sample might be subject to is a detailed pressure-volume-temperature ("PVT") analysis undertaken at a fixed land based facility equipped to undertake such a study. As both the facilities and their equipment are well known to those familiar with the art, they will not be elaborated on here. Alternatively, on-site analysis can also be undertaken right after samples have been collected and returned to the surface, or during transfer at the surface; however, severe space and time constraints attend any on-site analysis, and these tend to be limited in their offerings. An example of such on-site analysis would be the semi-detailed, quantitative, and unobtrusive analysis delivered by say Halliburton's Integrated Computation Element ("ICE") system.

Systems and methods described herein also may allow quantitative analysis of one or more components of a formation fluid by providing a weighted mixing fluid for mixing a formation fluid where the weighted mixing fluid includes a scavenger that reacts with one or more components of the formation fluid. The scavenger can be used to determine the quantity of an impurity in the formation fluid. The scavenger may be dissolved or dispersed in the weighted mixing fluid and in some aspects may function as a weighting agent for the weighted fluid.

The scavenger may be formed from a variety of materials, and may be any material that reacts with an impurity in the fluid sample to reduce or eliminate the presence of the free impurity or to selectively absorb the impurity. Formation fluids often include impurities such as $H_2S$ and mercury, so in the oilfield industry a scavenger may be any material that would react with one of those impurities or any other known impurity. For example, if the impurity is $H_2S$, the scavenger may be composed of alkali hydroxides, such as sodium hydroxide or potassium hydroxide; metals such as iron, zinc, copper, or silver; metal salts such as ferrous gluconate, zinc salts, or silver salts; organic scavengers such as reactive aldehydes (including formaldehyde, acrolein, and glyoxal); and amines, including alkanolamines such as ethanolamine and diethanolamine.

When the weighted mixing fluid and formation fluid are combined, the scavenger is free to interact with the formation fluid. In some methods, the volume of the weighted fluid is selected to provide enough scavenger material to react with a maximum estimated amount of a target impurity, such as $H_2S$, so the scavenger will react with the entire amount of the target impurity in the formation fluid sample. The sample chamber may be rocked to move the weighted fluid including the scavenger within the sample compartment, causing the fluids to mix and causing the scavenger to come into contact with the formation fluids and any unreacted impurity therein, furthering any reaction between the scavenger and the impurity. After a sufficient time, when reaction is complete, usually within four hours and almost always within twenty-four hours, the fluid sample may be analyzed to determine the concentration of impurity within the well fluid.

After mixing is accomplished, one or both of the weighted mixing fluid and the sample formation fluid may be analyzed to determine the concentration of the impurity within the formation fluid. Illustrative methods of using a scavenger to determine concentration of an impurity include measuring the concentration of a byproduct created when the scavenger reacts with the impurity; measuring the concentration of any leftover scavenger that did not react with the impurity; and causing an additional reaction within the fluid sample to extract the impurity from the byproduct followed by direct measurement of the concentration of the impurity. These methods are described in more detail below.

The process for analyzing a sample may vary significantly depending on the type of scavenger used, and whether the reaction between the scavenger and the impurity is a regenerative or non-regenerative reaction. As referenced herein, a regenerative reaction is a reaction with a contaminant that can be undone in a lab environment to determine the concentration of the contaminant by measuring it directly. For example, in the case of $H_2S$, regenerative scavengers may include sodium hydroxide (NaOH) and potassium hydroxide (KOH), and alkanolamines, such as ethanolamine and diethanolamine. Such scavengers react with $H_2S$ to form compound bonds that can be displaced by, for example, heating or gas stripping. Upon displacement of the bonds, the concentration of the $H_2S$ may be accurately measured using any suitable method, such as gas chromatography or inductively coupled plasma atomic emission spectroscopy (ICP-AES).

Metal scavengers such as iron, zinc, copper, and silver that react with $H_2S$ to produce insoluble sulfides are also examples of regenerative scavengers. Using such scavengers, the solid can be recovered by filtration and measured by any number of techniques, including treatment to solubilize the metal, the concentration of which may be determined using ICP, using colourimetric methods, or electrochemically. Similarly, strong acid can be used to regenerate the $H_2S$, which is measured using an appropriate technique. Organic scavengers can also be used, and the concentration of either the reagent or byproduct of the reaction between the reagent and $H_2S$ can be measured to determine the concentration of $H_2S$ in the fluid sample.

By using a regenerative scavenger to react the $H_2S$ with the scavenger during sampling and regenerating the $H_2S$ with a secondary reaction prior to analysis, $H_2S$ concentrations may be directly measured in a lab environment while ensuring that the volatile $H_2S$ gas is not reacted during transport from the sample site. This may be especially useful in cases where only a small amount of $H_2S$ is present, for example less than 20 ppm or between 20 and 50 ppm, and the $H_2S$ may not be otherwise detectable.

In aspects, a non-regenerative scavenger may be applied as a trap or converter material prior to analysis of the fluid sample. Examples of non-regenerative scavengers include certain implementations of metal scavengers such as silver, and other oxidizers. Such other oxidizers may include potassium permanganate ($KMnO_4$), and potassium dichromate ($K_2Cr_2O_7$). These types of reagents oxidize sulfide to sulfate, a byproduct which may subsequently be analyzed to determine the concentration of $H_2S$ in the fluid sample as it was taken from the formation. Other oxidizers, such as peroxide, persulfate, percarbonate, cerium salts, chlorate, or bromate may be used as scavengers in a similar manner.

In aspects, ferric ions ($Fe^{+3}$) may be used as scavengers that react with the H2S to form ferrous iron ($Fe^{+2}$), elemental sulfide, and hydrogen gas. The fluid sample may be assayed to determine the concentration of ferrous iron, which in turn would indicate the initial concentration of $H_2S$.

Applying similar methods, triazines may be reacted with the $H_2S$ to form dithiane and trithiane, and polyamines may be catalyzed by quat salts. Other scavenger materials may include reactive aldehydes such as acrolein, gluteraldehyde, and glyceraldehyde, silver or ferrous metal charged ion exchange resins, amine or sodium form ion exchange resins, and other solid adsorbents such as proprietary macroreticular resins, including Amberlite XAD-2, Carbotrap, Carbopak, or Carbosieve available from Sigma Aldrich. While $H_2S$ is used to exemplify these methods, one of skill in the art could adapt the scavengers and the analytic techniques for other impurities.

In aspects, the weighted fluid includes a sufficient amount of scavenger to react with a maximum estimated amount of $H_2S$ that may be included within the sample fluid. For example, the scavenger may be NaOH, which has a mole weight of 40 g/mole. $H_2S$ has a mole weight of 34.08 g/mole, and in this example, the NaOH and $H_2S$ are reacted to form $Na_2S$ and $H_2O$. It follows that at least approximately 2.34 (or 2(40/34.08)) grams of NaOH per gram of $H_2S$ is needed to react with the $H_2S$. Thus, if it is estimated that a sample compartment may contain at most 1.0 grams of $H_2S$, an operator may select a fluid volume sufficient to contain scavenger at least 2.34 grams of scavenger to ensure that all $H_2S$ in the sample compartment is reacted.

In aspects, the disclosure is directed to methods of mixing fluids. Ideally, the methods reduce wear of a wall in a vessel as compared to using solid mixing tools. The methods include steps of contacting in a vessel a first fluid comprising a weighted phase and a second fluid comprising a mixture of two or more materials, and moving the vessel to cause the first fluid to mix the second fluid. The vessel may be moved by rocking, or by any other method that causes the first fluid to mix the second fluid. The first fluid has an API gravity less than the API gravity of the second fluid. In aspects the first fluid has an API gravity less than about 10°, preferably less than about 9.0°, more preferably less than about 8.0°, even more preferably less than about 7.0°, and most preferably less than about 5.0°.

In aspects the weighted phase comprises a saturated or supersaturated aqueous solution or colloid. In aspects the saturated or supersaturated aqueous solution is selected from the group consisting of a salt solution, a sugar solution, a urea solution, a glycerol solution, a methylsulfonylmethane solution, and combinations thereof.

In aspects, the weighted aqueous phase includes a salt that is any combination of cation and anion that is soluble in water. In aspects the salt is formed from a cation selected from the group consisting of: $Na^{+1}$, $K^{+1}$, $Ca^{+2}$, $Zn^{+2}$, $Cs^{+2}$; and $Ba^{+2}$ and an anion selected from $SO_4^{-2}$, $Cl^{-1}$, $Br^{-1}$, $F^{-1}$, $I^{-1}$, and formate. In aspects the salt is potassium bromide.

In aspects, the weighted aqueous phase includes a sugar that is selected from the group consisting of C5 saccharides, C6 saccharides, and combinations thereof.

In aspects, the weighted aqueous phase further comprises at least one demulsifier.

In aspects the second fluid is a sample from a wellbore, including at least one oil or gas, and the weighted aqueous phase is a saturated or supersaturated aqueous solution or colloid. In one aspect the second fluid includes crude oil.

In aspects, the second fluid comprises impurities. Where the second fluid is a formation fluid extracted from a wellbore, those impurities may include, but are not limited to $H_2S$ and/or mercury. Impurities may be present in trace amounts.

In some aspects, the weighted aqueous phase is inert and the method does not alter the concentration of materials in the second fluid.

In some aspects, the second fluid comprises impurities and the weighted aqueous phase includes a scavenger that reacts with those impurities. In aspects the second fluid is a formation fluid extracted from a wellbore, the impurities include $H_2S$ and/or mercury, and the scavenger includes a material that reacts with those impurities. In aspects, the scavenger includes an alkali hydroxide, such as sodium hydroxide and potassium hydroxide; a metal such as iron, zinc, copper, or silver; a metal salt such as ferrous gluconate, zinc salts, or silver salts; an organic scavenger such as reactive aldehydes (including formaldehyde, acrolein, and glyoxal); or an amine, including alkanolamines such as ethanolamine and diethanolamine.

In aspects the weighted aqueous phase is present at a level of about 1% by volume to about 25% by volume, but may be present at much higher levels, up to about 50% by volume, 60% by volume, 70% by volume, 80% by volume, 90% by volume based on the total volume of the mixture of fluids.

In aspects the vessel includes a wall made from at least one material selected from stainless steel, austenitic nickel-chromium-based superalloy, cobalt, titanium, and combinations thereof.

In aspects the wall of the vessel is porous and is optionally coated. In aspects the wall is coated, and said coating comprises at least one material selected from the group consisting of a silicon-based coating (such as, for example, Sulfinert™ treatments), a ceramic-based coating (such as, for example, Tech-12™ treatments), and combinations thereof.

In aspects the vessel is a sample container, such as a sampling container used downhole or at the surface to collect hydrocarbon samples. In aspects the sample container is a long-term storage container.

In aspects the methods further include separating said first fluid from said second fluid and, optionally, reusing the first fluid in a similar process. In aspects the separating may be accomplished by any suitable means, for example gravity-based separation technique, a chemical affinity-based separation technique, or a combination thereof.

The present disclosure also encompasses methods for analyzing a fluid sample where the methods include contacting in a vessel a first fluid comprising a weighted aqueous phase and a second fluid comprising a mixture of at least one fluid and at least one impurity. The weighted aqueous phase is a saturated or supersaturated aqueous solution or colloid and includes a scavenger that can react with the at least one impurity. The weighted aqueous phase has an API gravity less than the API gravity of the second fluid. The method includes moving the vessel to cause the first fluid to mix the second fluid, whereby the scavenger can react with the at least one impurity, and determining the concentration of the at least one impurity.

In aspects, determining the concentration of the at least one impurity comprises measuring the concentration of a byproduct created when the scavenger reacts with the impurity.

In aspects, determining the concentration of the at least one impurity comprises regenerating the impurity and measuring the amount of impurity.

The present disclosure also encompasses systems for mixing fluid samples. In aspects a system comprises a vessel, a first fluid including a weighted aqueous phase, and a second fluid including a hydrocarbon fluid extracted from a wellbore. The weighted aqueous phase is a saturated or supersaturated aqueous solution or colloid. The weighted aqueous phase has an API gravity less than the API gravity of said second fluid.

In aspects a system for mixing fluid samples includes a first fluid including a weighted aqueous phase that is a saturated or supersaturated aqueous solution or colloid and that includes a scavenger, and a second fluid including a hydrocarbon fluid extracted from a wellbore that includes an impurity that can react with the scavenger.

When ranges are used herein for physical properties, such as molecular weight, or chemical properties, such as chemical formulae, all combinations, and sub-combinations of ranges of specific aspects therein are intended to be included.

The compositions, methods, and systems described herein are described in sufficient detail to enable those skilled in the art to practice the invention, and it is understood that other compositions, methods, and systems may be utilized and that logical structural, mechanical, electrical, and chemical changes may be made without departing from the spirit or scope of the invention. To avoid detail not necessary to enable those skilled in the art to practice the methods described herein, the description may omit certain information known to those skilled in the art. The present disclosure is, therefore, not to be taken in a limiting sense, and the scope of the invention is defined only by the appended claims, which should be interpreted to encompass all such equivalents and variations as fall within the true spirit and scope of the disclosure.

What is claimed is:

1. A method of mixing a fluid, comprising:
    contacting in a vessel:
        a first fluid, and
        a second fluid comprising a mixture of two or more materials; and
    moving the vessel to cause the first fluid to mix the second fluid,
        wherein the first fluid has an American Petroleum Institute ("API") gravity less than the API gravity of the second fluid, wherein the first fluid comprises a weighted aqueous phase comprising a saturated or supersaturated aqueous solution or colloid.

2. The method of claim 1, wherein the first fluid has an API gravity less than about 10°.

3. The method of claim 1, wherein said, saturated or supersaturated aqueous solution is selected from the group consisting of a salt solution, a sugar solution, a urea solution, a glycerol solution, a methylsulfonylmethane solution, a cesium formate solution, and combinations thereof.

4. The method of claim 3, wherein said salt comprises:
    a cation selected from the group consisting of: $Na^{+1}$, $K^{+1}$, $Ca^{+2}$, $Zn^{+2}$, $Cs^{+2}$; and $Ba^{+2}$; and an anion selected from $SO_4^{-2}$, $Cl^{-1}$, $Br^{-1}$, $F^{-1}$, $I^{-1}$, and formate.

5. The method of claim 4, wherein said salt comprises potassium bromide.

6. The method of claim 1, wherein said first fluid further comprises at least one demulsifier.

7. The method of claim 1, wherein said second fluid comprises a fluid extracted from a wellbore during a wireline formation testing, measuring while drilling, logging while drilling, or drill stem testing operation.

8. The method of claim 7, wherein the second fluid comprises crude oil.

9. The method of claim 1, wherein said second fluid is present at a level of about 1% by volume to about 25% by volume, based on the total volume of said mixture.

10. The method of claim 1, wherein the weighted aqueous phase is inert.

11. The method of claim 1, wherein the weighted aqueous phase includes a scavenger.

12. The method of claim 1, where moving comprises rocking.

13. The method of claim 1, further comprising separating the first fluid from the second fluid.

14. The method of claim 13, wherein separating comprises a separation method selected from the group consisting of a gravity-based separation technique, a chemical affinity-based separation technique, and a combination thereof.

15. A method of analyzing a fluid, comprising:
    contacting in a vessel:
        a first fluid comprising a weighted aqueous phase, and
        a second fluid comprising a mixture of at least one fluid and at least one impurity;
        wherein the weighted aqueous phase is a saturated or supersaturated aqueous solution or colloid,
        wherein the weighted aqueous phase comprises a scavenger that can react with the at least one impurity, and
        wherein the weighted aqueous phase has an API gravity less than the API gravity of the second fluid;
    moving the vessel to cause the first fluid to mix the second fluid, whereby the scavenger can react with the at least one impurity; and
    determining the concentration of the at least one impurity.

16. The method of claim 15, wherein determining the concentration of the at least one impurity comprises measuring the concentration of a byproduct created when the scavenger reacts with the impurity.

17. The method of claim 15, wherein determining the concentration of the at least one impurity comprises regenerating the impurity and measuring the amount of impurity.

18. A system comprising:
    a vessel,
    a first fluid comprising a weighted aqueous phase, and
    a second fluid comprising a hydrocarbon fluid extracted from a wellbore,
        wherein said weighted aqueous phase is a saturated or supersaturated aqueous solution or colloid, and
        wherein said weighted aqueous phase has an API gravity less than an API gravity of the hydrocarbon fluid.

19. The system of claim 18,
    wherein said second fluid comprises an impurity, and
    wherein said, weighted aqueous phase comprises a scavenger able to react with the impurity.

* * * * *